United States Patent [19]
Beiting

[11] Patent Number: 5,579,166
[45] Date of Patent: Nov. 26, 1996

[54] PRECISION OPTICAL PULSE TRAIN GENERATOR

[76] Inventor: Edward J. Beiting, 2 Sausalito Cir. East, Manhattan Beach, Calif. 90266

[21] Appl. No.: 423,178

[22] Filed: Apr. 18, 1995

Related U.S. Application Data

[62] Division of Ser. No. 259,287, Jun. 13, 1994, which is a continuation of Ser. No. 962,793, Aug. 5, 1992, abandoned.

[51] Int. Cl.$^6$ .......................... G02B 27/14; G02B 27/10
[52] U.S. Cl. .......................... 359/636; 359/629; 359/618
[58] Field of Search .................................. 359/636, 618, 359/629, 619, 623, 626, 634

[56] References Cited

U.S. PATENT DOCUMENTS

| | | | |
|---|---|---|---|
| 3,662,106 | 5/1917 | Buller | 359/618 |
| 3,699,344 | 10/1972 | Rutz | 359/618 |
| 3,879,109 | 4/1975 | Thomas | 359/629 |
| 3,986,130 | 10/1976 | Soures | 359/629 |
| 4,057,725 | 11/1977 | Wagner | 250/360 |
| 4,061,985 | 12/1977 | Siebert | 359/264 |
| 4,093,964 | 6/1978 | Aughton | 359/618 |
| 4,344,671 | 8/1982 | Lang | 359/618 |
| 4,386,854 | 6/1983 | Byer | 356/438 |
| 4,613,206 | 9/1986 | Franchetti | 359/629 |
| 4,659,185 | 4/1987 | Aughton | 359/629 |
| 4,871,232 | 10/1989 | Grinberg | 359/618 |
| 4,986,654 | 1/1991 | Meijer | 356/43 |
| 5,448,417 | 9/1995 | Adams | 359/856 |

Primary Examiner—Georgia Y. Epps
Assistant Examiner—Ricky Mack

[57] ABSTRACT

A design for a fast absorption optical tomography instrument is disclosed. The subject invention is capable of generating 100 projections of 100 elements each in less than 200 ns. It comprises and optical pulse generator, a tomography ring with temporally multiplexed fiber-optic fan-beam sources and fast detectors, and data acquisition electronics. A single short pulse (<10 ns) of radiation tuned to an absorption transition of the chemical species of interest produces a cross sectional image of concentration. Supplying two such pulses to the instrument can yield simultaneous quantitative images of temperature and absolute concentration in fields with temperature inhomogeneities. Additional pulses lead to concentration images of additional species.

11 Claims, 6 Drawing Sheets

PRECISION OPTICAL PULSE TRAIN GENERATOR

STATEMENT OF GOVERNMENT INTEREST

The invention described herein may be manufactured and used by or for the Government of the United States for governmental purposes without the payment of royalty therefor.

REFERENCE TO RELATED APPLICATION

This application is a divisional of application Ser. No. 08/259,287 filed Jun. 13, 1994 which is a continuation of application Ser. No. 07/962,793 filed Aug. 5, 1992, which is abandoned, entitled "Fast Optical Absorption Tomography Apparatus and Method".

SUMMARY OF THE INVENTION

An absorption tomography instrument is constructed using an optical pulse generator, a tomography ring, and data acquisition electronics. The ring includes time-multiplexed, fiber-optic, fan-beam sources and fast, large area detectors. The fan-beam sources are sequentially activated in groups to minimize the number of detectors required to achieve a given resolution. The instrument is capable of acquiring 100 projections of 100 elements each, in less than 200 ns. The instrument can be tailored to particular application.

BACKGROUND OF THE INVENTION

1. Field of the Invention

This invention relates generally to techniques of visualizing planar fields of chemical concentration and/or temperature in rapidly moving gases and more particularly to the measurement of these quantities in turbulent flow.

2. Description of the Prior Art

The instantaneous three-dimensional characterization of reacting, turbulent flows is the ultimate goal of optical diagnostics of gases. Complete understanding of this environment requires simultaneous, spatially resolved measurements of both chemical and fluid dynamic parameters. Much progress toward this goal has been made using Rayleigh and Mie scattering. However, these scattering techniques cannot differentiate chemical species.

Planar laser induced fluorescence (PLIF) is the technique that competes most directly this proposed method because it is fast, capable of high spatial resolution, and can differentiate chemical species. FIG. 1A illustrates the difference in implementation between PLIF and optical absorption tomography. PLIF operates by crossing a flow of gas 2 with a sheet of light 4 tuned to an absorption of the chemical species of interest. A fraction of the molecules are excited from the ground state to an excited state of the molecule. PLIF images the emitted light 6 with an 2D detector 8 (electronic camera) and attempts to infer the magnitude of $N_0$ from this light. Tomography measures the amount of light absorbed across the sheet of light 4 using a one dimensional detector 10 creating a "projection." Projections must be measured at many angles around the flow and these data are used to "reconstruct" a cross sectional map of the concentration using computer algorithms.

PLIF suffers from collisional quenching that can render its measurements difficult to interpret quantitatively in practical flows. This is illustrated using FIG. 1B. Here, $N_0$ is the number of molecules in the ground state (concentration to be measured) and $N_1$ is the number of molecules excited by the laser radiation E. The number of molecules excited ($N_1$) exits this upper state via two channels: collisional de-excitation (quenching) Q and fluorescence F to an intermediate state in which light is emitted. The difficulty lies in the fact that the collisional deactivation rate Q generally is not known and this rate is many times larger than the deactivation rate due to fluorescence F (except in very low pressure flows). In optical absorption tomography the absorption depends only on $N_0$ and hence is independent of the unknown quenching rate Q.

Tomography was first suggested for the study of reacting flows by R. Goulard and P. J. Emmerman, *Topics in Current Physics*, 20; *Inverse Scattering Problems in Optics*, H. P. Baltes, ed., Springer-Verlag, New York, p. 215, (1980). However, even though optical tomography can be applied to a wide class of important fluid dynamic problems, implementation has been limited to a few proof-of-principle studies. For example, R. Goulard and S. R. Ray, *Advances in Remote Sensing Retrieval Methods*, A. Deepak, H. E. Fleming, and M. T. Chahine, eds., A. Deepak Publishing, Hampton, Va. (1985) and S. R. Ray and H. G. Semerjian, Paper 83-1553, AIAA 18th Thermophysics Conference, Montreal, Canada (1983) have measured temperature and OH concentration fields in a steady-state, premixed flame with a continuous wave (cw) ring dye laser. Absorption experiments used fan beam geometry and either an $Ar^+$ laser through a rotating mirror to study an iodine plume (K. E. Bennett, G. W. Faris, and R. L. Byer, *Appl. Opt.* 22, 2678–2685 (1984); K. Bennett and R. L. Byer, *Opt. Lett.* 9, 270–272 (1984)) or a lamp source directed through a rotating chlorine jet (G. W. Faris and R. L. Byer, *Opt. Lett* 7, 413–415 (1986)) to create projections. More recently, R. Synder and L. Hesselink, *Appl. Opt.* 24, 4046–4051 (1985), demonstrated a novel configuration using holographic optical elements and a rotating mirror.

These studies share common shortcomings: they all rely on rotating elements and cw lasers, thus restricting measurements to a millisecond time scale. In order to be effective, a species-specific optical tomography instrument capable of imaging turbulent structure and temperature in fast reacting flows must collect data on a microsecond time scale.

The time resolution required of an instrument is determined by the necessity to freeze a resolution element. The size of the resolution element should approach the smallest space scale of the turbulence. For flow velocities not much greater than 100 m/s, the smallest space scale, or eddy, will be approximately 1 mm. If an element is considered to be stationary if it does not move more that 10% of its size during the measurement, all data must be collected in $10^{-6}$ s. As the velocity decreases and the scale size increases, this time increases considerably. Finally, about 10,000 pieces of data (pixels) should be collected during that time to create a meaningful image.

The primary object of this invention is therefore an absorption tomographic instrument capable of imaging one or more chemical species and/or temperature with sufficient temporal and spatial resolution to resolve turbulent structure in high speed gaseous flows. A related object of the invention is to capture nominally 100 projections of 100 elements each on a microsecond time scale.

DETAILED DESCRIPTION OF THE PREFERRED EMBODIMENT

Figure 1A:
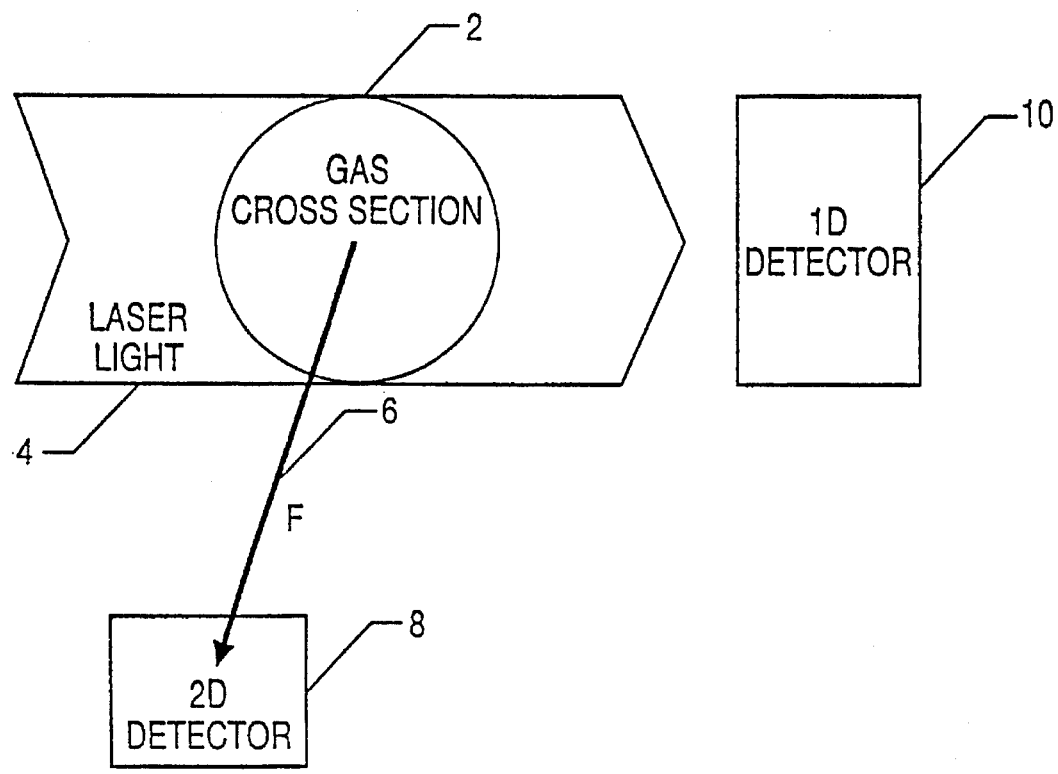
FIG. 1A and FIG. 1B illustrate the principles of planar laser induced fluorescence (PLIF) and absorption tomography.
Figure 1B:
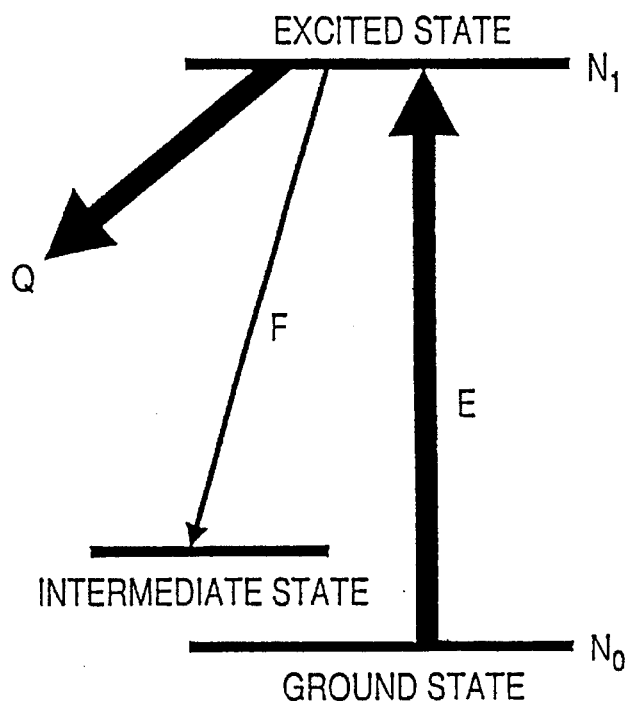
Figure 2:
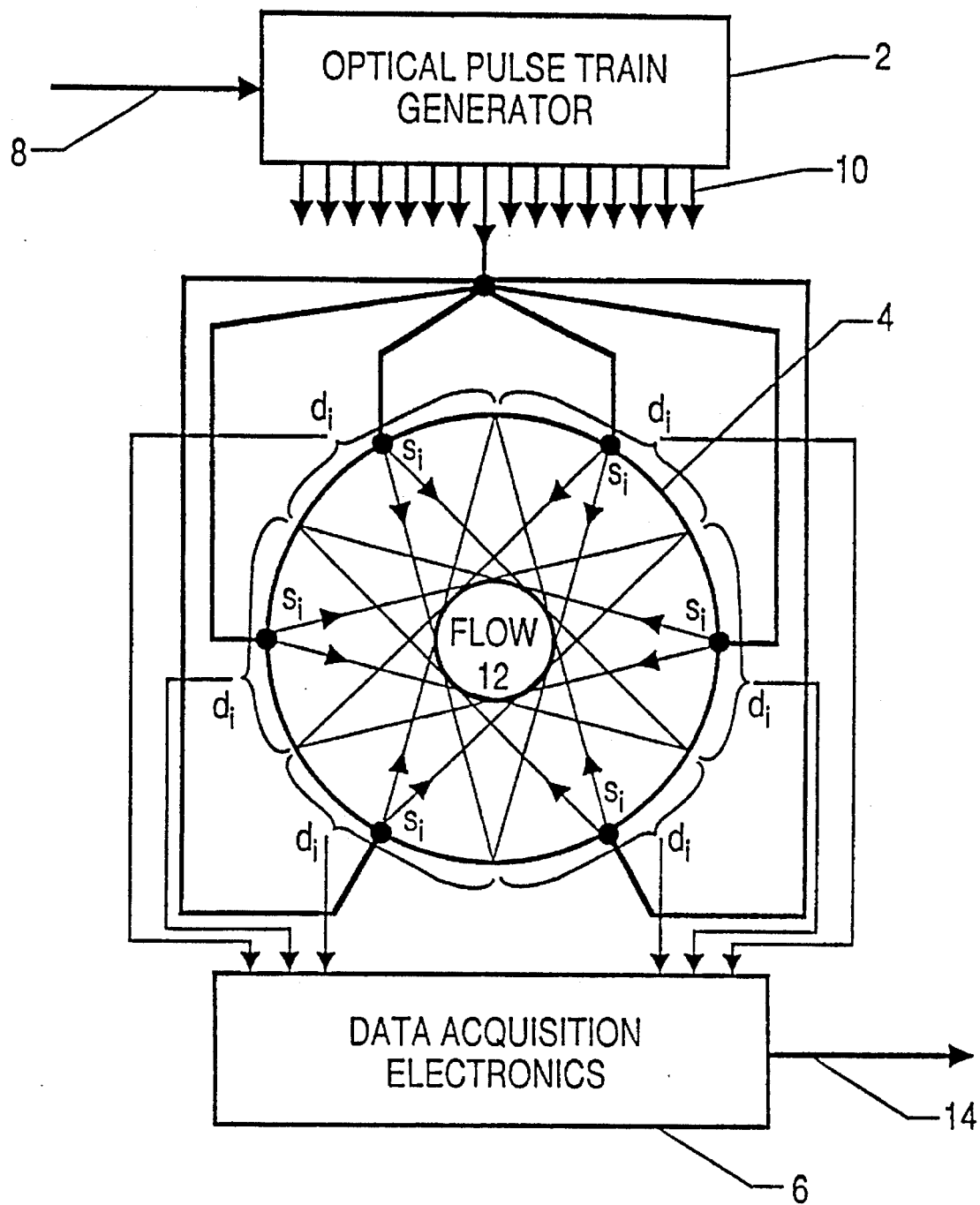
FIG. 2 shows the three principal components of the invention: an optical pulse train generator (OPTG); a tomography ring that surrounds the flow under investigation; and data acquisition electronics.

FIG. 2 illustrates the primary components of the invention. The invention comprises an optical pulse train generator (OPTG) 2, a tomography ring 4, and data acquisition electronics 6. In general, the OPTG 2 creates a series of n identical, equally spaced pulses from a single input laser pulse 8. For FIG. 2, n=16. Each pulse in the series is transmitted by means of a fiber-optic cable 10 that branches to m positions symmetrically placed around the tomography ring that surrounds a flow 12 under study. For FIG. 2, m=6. Each fiber optic is terminated with a microlens that casts the light into a flat fan. The fibers and microlenses thus create a total of n×m fan-beams sources $s_i$. Accordingly, sets of m fans are sequentially activated n times creating a total of n×m fans around the ring.

A series of detectors $d_i$ completely surrounding the flow is also located on the tomography ring 4 slightly above or below the fan beam sources. As each source $s_i$ illuminates the flow, the light is registered only by the detectors $d_i$ located on the opposite side of the ring in the path of the light from that fan. Information from the detectors is routed to the data acquisition electronics 6 in the form of a series of equally timed pulses of varying voltage. The electronics converts of the voltage pulses to numbers (i.e. digitizes them) using electronic sampling technology. The output data 14 are sent to a computer that reconstructs a cross-sectional view and displays it graphically. Each of the primary components is discussed in more detail below.

Optical Pulse Train Generator (OPTG) 2

The principle of the OPTG 2 is path-length delay and wavefront division. However, relaying even a well collimated laser beam between two plane retroreflectors and using a variable reflectivity beam splitter as an output coupler lead to impractical beam diameters and inconvenient path lengths after a few pulses. The device introduced here, based on the stable geometry of a White cell [J. U. White, *J. Opt. Soc. Am.* 32, 285–288 (1942)], avoids these problems.

Figure 3:
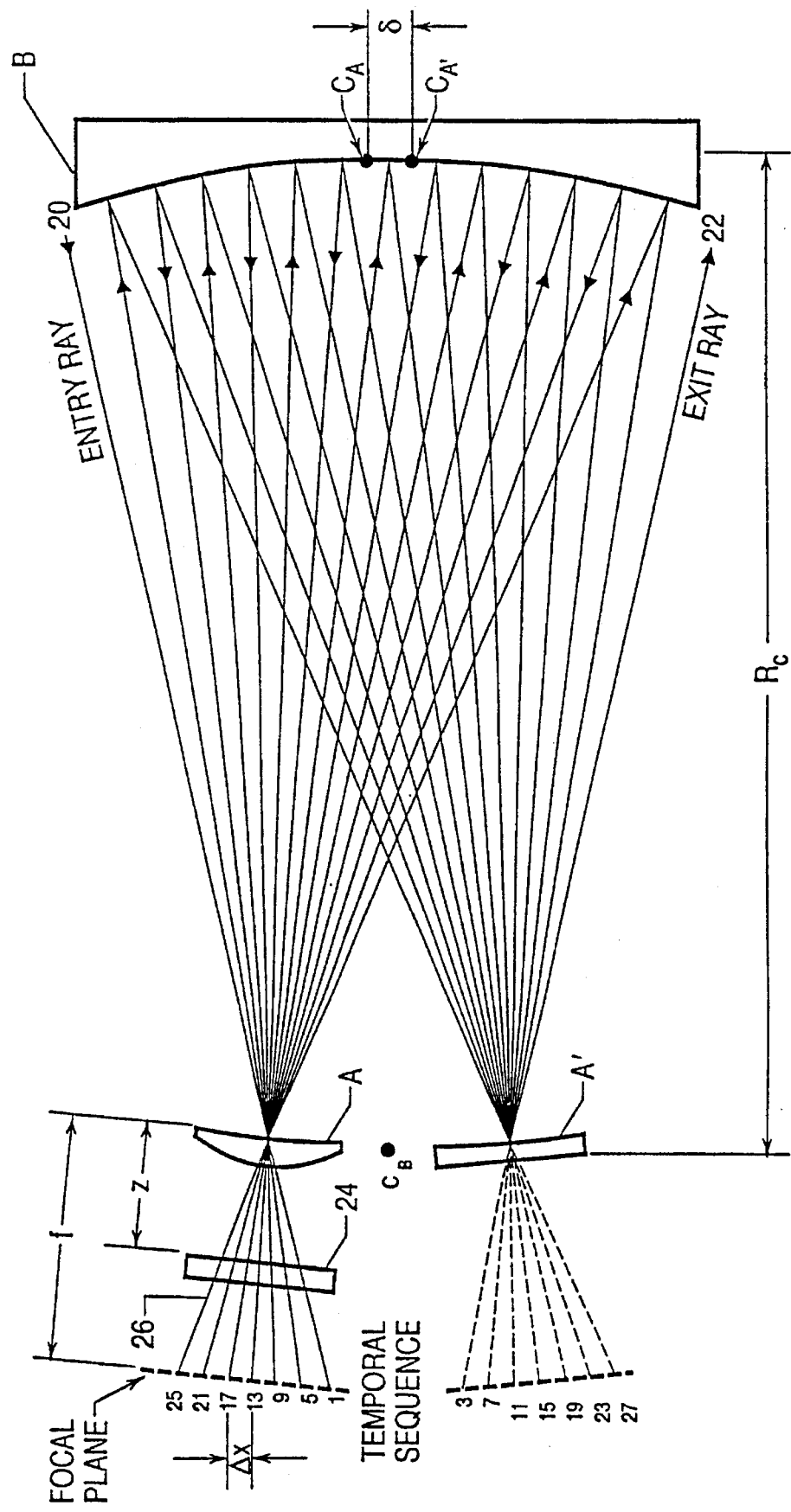
FIG. 3 shows the geometry used to generate a series of pulses separated by equal time intervals.

FIG. 3 illustrates a modified White cell. A classical White cell comprises entrance 20 and exit 22 slits, and three spherical mirrors A,A' and B, with equal radii of curvature, $R_c$. The slits 20, 22 lie at opposite edges of mirror B, a distance $R_c$ from $C_B$, its center of curvature. The centers of curvature of mirrors A and A' lie symmetrically about the center of mirror B at points $C_A$ and $C_{A'}$. Light diverging from the entrance slit 20 is collected and focused by mirror A to position 2 on the surface of mirror B. This light then diverges to mirror A', which focuses it to position 4 on the surface of mirror B, etc. The conjugate object and image rays striking mirror A (or A') make equal angles with the line joining the center of mirror A (or A') with $C_A$ (or $C_{A'}$). The focal points on mirror B are separated by the distance between the centers of curvature, $\delta = \overline{C_A C_{A'}}$. Symmetrically pivoting and reducing the separation between mirrors A and A' to decrease the separation $\delta$ increases the number of traverses through the cell. The entrance slit must be placed a distance $(n+\frac{1}{2})\delta$ from $C_A$ (where n is an integer) to have the final beam pass through a symmetrically placed exit slit. Placing the entrance slit a distance $n\delta$ from $C_A$ results in ray positions on mirror B separated by $2\delta$ as the ray retraces itself along the same paths in the opposite direction.

To use this geometry for the OPTG 2, the entrance and exit slits are eliminated and the output of a laser is introduced directly at the entrance slit position. Although the divergence of the beam is not critical, the beam will be considered to be reasonably collimated in the following discussion. The diameter of mirrors A and A' and the height of mirror B need only be large enough to accommodate the beam diameter. All beams traveling toward mirrors A and A' are collimated (i.e., have the divergence of the original beam). All beams traveling to mirror B converge to waists located near the center of the cell and subsequently diverge to mirror B. This geometry can produce a train of equally spaced pulses because the sum of the optical paths of any pair of left and right traveling beams always equals $2R_c$. Therefore, beams at the surface of mirror B are temporally separated by multiples of $2R_c/c$ and those on mirrors A and A' are separated by multiples of $4R_c/c$, where c is the speed of light. Note that this configuration is useful for high power laser applications since the beam waists are near the center of the cell, minimizing the intensity at the surface of the mirrors.

Although any or all of the mirrors can be used as output couplers, it is particularly convenient to use mirror A to extract the train of pulses. The concave face of mirror A is uniformly covered with a partially reflecting coating; the back is given a radius of curvature shorter than that of its reflecting surface to create a positive meniscus lens of focal length f. The collimated beams passing through this output coupler form a fan of beams that are individually focused along a straight line a distance f behind mirror A. The total number of points (pulses), in this line is $$n_p = \frac{L_B + \delta}{2\delta} \quad (1)$$

where $L_B$ is the length of mirror B. The maximum number of pulses, $n_p^{max}$, that can exit this output coupler is $L_B/d$ where d is the diameter of the entry beam. The foci are separated at the focal plane by $$\Delta x_{focus} \approx 2f\delta/R \approx \frac{4R_o\delta}{R_c + R_o} \quad (2)$$

where $R_o$ is the radius of curvature of the outer surface of the output coupler A.

The amplitudes of the pulses exiting the output coupler A are not constant and are a strong function of the reflectivities. If $r_A$, $r_B$, and $r_{A'}$ are the reflectivities of mirrors A, B, and A', respectively, then the fractional decrease in amplitude from pulse-to-pulse is $$\frac{I_i - I_{i+1}}{I_i} = 1 - r_A r_B^2 r_{A'} \quad (3)$$

where $I_i$ is the amplitude of the ith pulse. The ratio of the amplitude of the last-to-first pulse for a train of $n_p$ pulses is $(r_A r_B^2 r_{A'})^{n_p+1}$. If the entrance pulse has an amplitude of $I_0$, then the efficiency of the OPTG is $$\sum_{i=1}^{n_p} I_i/I_0 = (1 - r_A) \left[ \frac{1 - (r_A r_B^2 r_{A'})^{n_p}}{1 - r_A r_B^2 r_{A'}} \right]. \quad (4)$$

These expressions assume the absorption and scatter of the output coupler are negligible.

A train of pulses of equal amplitude can be obtained at the expense of efficiency by inserting a variable neutral density filter 24 in the fan 26 of output beams. For constant spacing, $\Delta z$, between the adjacent outputs, the constraint that all transmitted amplitudes be equal leads to an expression for the optical density of the filter that is linear in position with a slope of $\log(r_A r_B^2 r_{A'})\Delta z$. Accordingly, a train of pulses of equal amplitude can be produced by inserting a standard variable neutral density filter 24 normal to the central ray 13 of the output fan 26. Adjusting the distance z of the filter from the output coupler A selects the proper slope, and adjusting its position normal to the central ray 13 selects the correct intercept.

Figure 4:
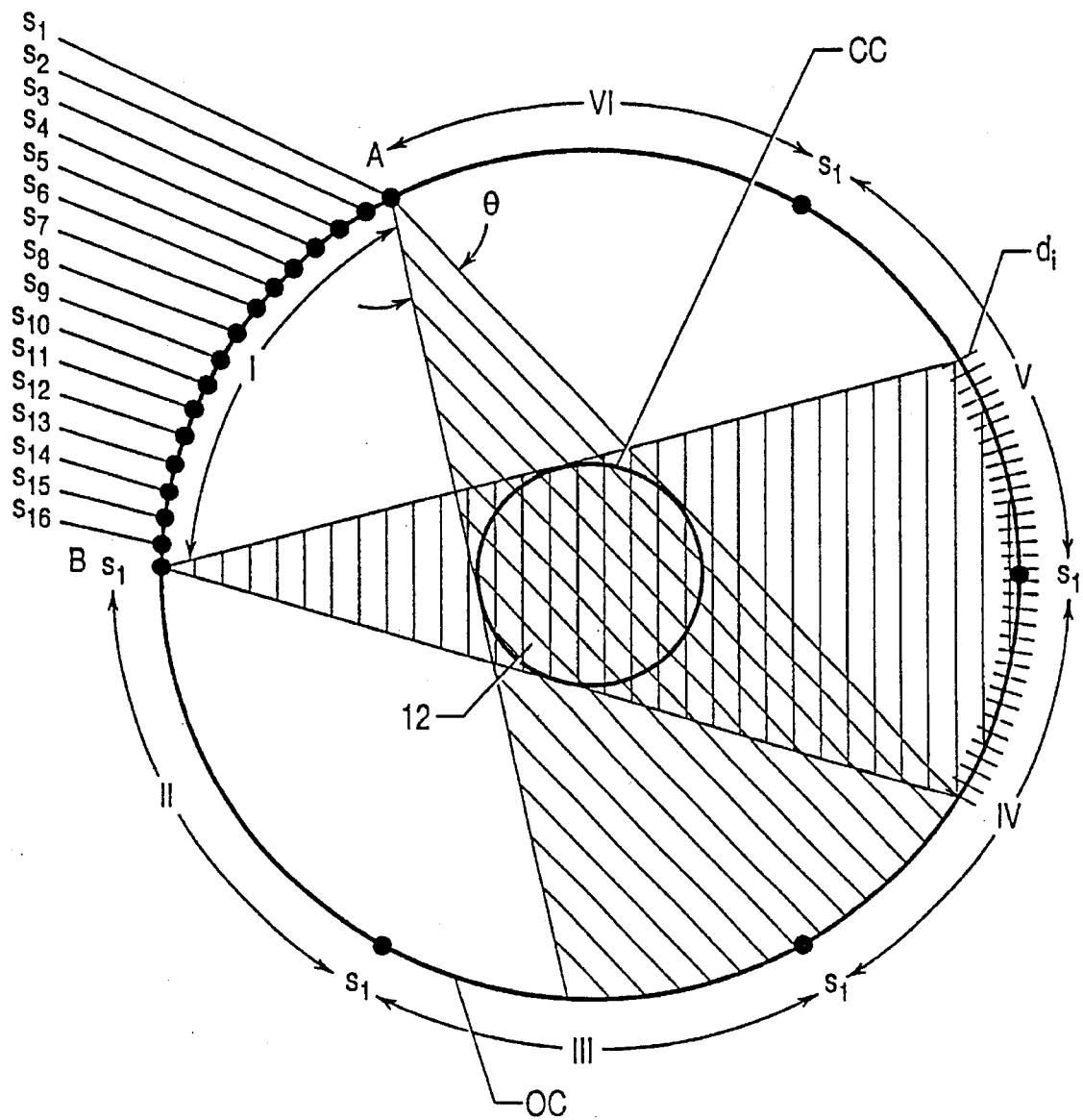
FIG. 4 is a schematic illustration a 96-fiber, 16 times multiplexing implementation of the instrument.

Tomography Ring 4:

FIG. 4 illustrates the geometry of the tomography ring. The center circle CC represents the cross section of the flow 12 to be investigated. The circumference of the outer circle OC describes a locus of point sources organized into separate sectors I, II .... Each source $s_i$ consists of a diverging flat fan of light of angle θ. The rays from each source pass through the probed region 12 and terminate on a series of detectors $d_i$ also located on the outer circle OC. If the sources are separated by $\geq 2\theta$ (fans A and B), rays from their fans will not overlap on the opposite side of the circle, and a one-to-$n_d$ correspondence exists between the sources and detectors, where $n_d$ is the number of detectors in each fan.

FIG. 4 depicts a geometry where six equally spaced fan sources $s_i$ could illuminate the entire circle of detectors $d_i$ without overlap. Now, consider placing fifteen additional sources $s_2$-$s_{16}$ in section I. Further, consider that these sources are activated sequentially so that source $s_1$ is emitting a fan of radiation at time $t_1$, source $s_2$ is emitting a fan of radiation at time $t_2$, etc., and that the time interval between each pulse of radiation is greater than the time any source is active. Then, a detector $d_i$ will receive the radiation from only one source at a time.

A train of these radiation pulses equally spaced in time is created from a single laser pulse 8 using the optical pulse train generator 2. Now consider that each pulse exiting the OPTG 2 is split so that it is carried to a source in sectors I–VI. This splitting is done effectively using fused fiber splitters (star couplers). Thus, the first pulse from the train is coupled to six fibers that carry the simultaneous pulses to the six locations marked $s_1$ on the circumference of the outer circle OC. The next pulse creates fans at the six $s_2$ locations, etc. In this way, 96 sources are created, but only 6 widely separated sources are active at any instant. In this example, 96 sources each illuminate 96 detectors, but only a total of 6×96=576 detectors is required. If the time interval between the pulses is 12 ns, the entire sequence is completed in 16×12 ns=196 ns.

More generally, the source ring radius required to fully sample a flow of radius $r_f$ is $$R = r_f \sqrt{2/(1 - \cos\theta_{fan})} \equiv F r_f, \quad (5)$$

where the fan angle is $$\theta_{fan} = \frac{\pi F_M}{N_f}, \quad (6)$$

$r_f$ is the radius of the flow cross section, $F = R/r_f$, $N_a$ ($=\pi/\theta_{fan}$) is the number of sectors (I, II ...), $N_f = N_a F_M$ is the total number of fan sources, and $F_M$ is the multiplexing factor (equal to 16 in the example above).

The spatial resolution of the instrument is approximately one-half the detector spacing if the detectors and sources reside on the same ring and the cross section is not under sampled in angular space. The total number of detectors, $N_d$, necessary as a function of detector spacing, w, is $$N_d = \frac{2\pi r_f F}{w} \approx \frac{4 r_f N_f}{w F_M}, \quad (7)$$

where F is defined by Eq. (5) and the approximation holds for small fan angles. Thus, the total number of detectors scales inversely with the multiplexing factor.

The multiple use of each detector allows a large number of equally spaced projections to be acquired while maintaining a large detector size. The width of the detectors is chosen to equal the detector spacing. There are several compelling reasons for using as large a detector size as possible consistent with the desired spatial resolution. These include increasing the signal-to-noise ratio and reducing the deleterious effects of diffraction, turbulence-induced beam steering, and laser speckle noise. Although reconstruction algorithms assume point detectors, the finite detector size does little to introduce artifacts into the reconstruction when algorithms based on the Radon operator are used in the backprojection algorithm to calculate the cross section of the flow.

From Eqs. (5–7), an expression for the width w available for the detector is found to be $$w = \frac{2\pi r_f}{N_a n_d} \sqrt{2/(1 - \cos(\pi/N_a))}. \quad (8)$$

Note that, for a single source-detector ring and a given resolution, the flow diameter dictates the detector spacing. If this is inconvenient for the size of the available detectors, the fan sources and detectors can be placed on separate concentric rings with different diameters. Higher spatial resolution for a given detector size can always be obtained by increasing the ratio of the detector-ring radius to fan-ring radius Data Acquisition and Output Electronics 6:

It is necessary to individually digitize the amount of charge exiting each pulse in each detector. However, if the shape of each pulse is identical, then the peak amplitude or voltage of each pulse is directly proportion to the charge of the pulse. Since all pulses created by the OPTG 2 are derived from the same laser pulse 8, all pulse shapes are identical. Although flash digitizers are available that can digitize pulses on a nanosecond time scale, they are expensive and have only 8 bit resolution. A more practical method to digitize the train of pulses emitted from each detector $d_i$ is to use fast sampling techniques and analog shift registers. Here, the peak of each pulse is sampled (the voltage sensed) and rapidly stored in one of a series of capacitors etched in a monolithic integrated circuit (IC). Since all the pulses are equally spaced in time, a single clock (pulse generator) is used to synchronize and set the sampling rate to the pulse rate. The information is collected and stored in the capacitors on a nanosecond times scale but is read out and digitized on a millisecond time scale, thus allowing high resolution (12 bit) digitization. Current technology allows 128 pulses from each of 32 different detectors to be processed by a single IC.

These digitized values (numbers) are rapidly stored in the memory of the computer controlling the instrument. The numbers can be subsequently stored on disk for later analysis, or if the computer is fast enough, processed and displayed in real time. It requires about 200 seconds per MIPS of computer speed to process 100 100-element projections using a backprojection tomographic algorithm and display 10,000 data points (pixels) graphically. Currently, a fast personal computer can do this in less than 10 seconds. Workstation-grade computers are about an order of magnitude faster.

A Preferred Embodiment

OPTG 2: Consider a baseline configuration for the OPTG with the following parameters: $R_c$=1 m; f=$R_c$/4; $L_B$=20 cm; $n_p$=16. Accordingly, $R_o$ is 14.3 cm, the temporal separation between pulses is 13.3 ns, and the spatial separation between foci is 2.9 mm. This baseline geometry is capable of generating 40 pulses using a laser beam with a diameter of 5 mm. If fewer than $n_p^{max}$/2 pulses are required, every other pulse can be used, thus halving the length of the cell for a given temporal separation between pulses or doubling the time interval for a given cell size. Further details of this configuration are described in E. J. Beiting, *Appl. Opt.* 31, 2642–2644 (1992).

The OPTG was tested by constructing 1–m ($R_c$=102 cm) and 2–m ($R_c$=203 cm) cells. Mirrors A' and B of each cell were double coated for high reflectivity (r>99% over two wavelength bands (305–350 nm and 490–550 nm). The reflectivity of the output couplers varied between 96.0 and 97.5% across these wavelength intervals. The back of mirror A had a radius of 14.0 cm, yielding paraxial focal lengths of 24 cm (≈$R_c$/4) for the 1–m cell and 26 cm (≈$R_c$/8) for the 2–m cell. Diameters of mirrors A and A' were 2.5 cm. Mirror B had a height of 2.5 cm and length of 20 cm. The calculated time separation between pulses for the 1–m and 2–m cells are 13.6 and 27.1 ns, respectively.

Figure 5A:
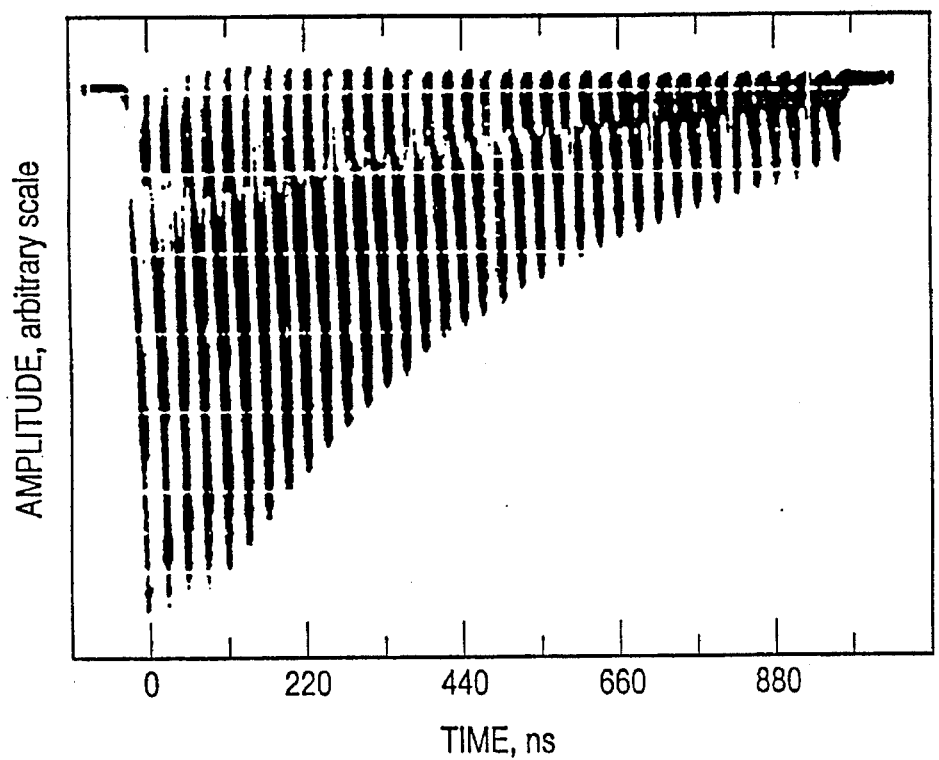
FIG. 5A shows a (negative) pulse train exiting a fast silicon photodiode created by a 2-m OPTG when a variable neutral density filter is not positioned in the expanding fan of output beams.
Figure 5B:
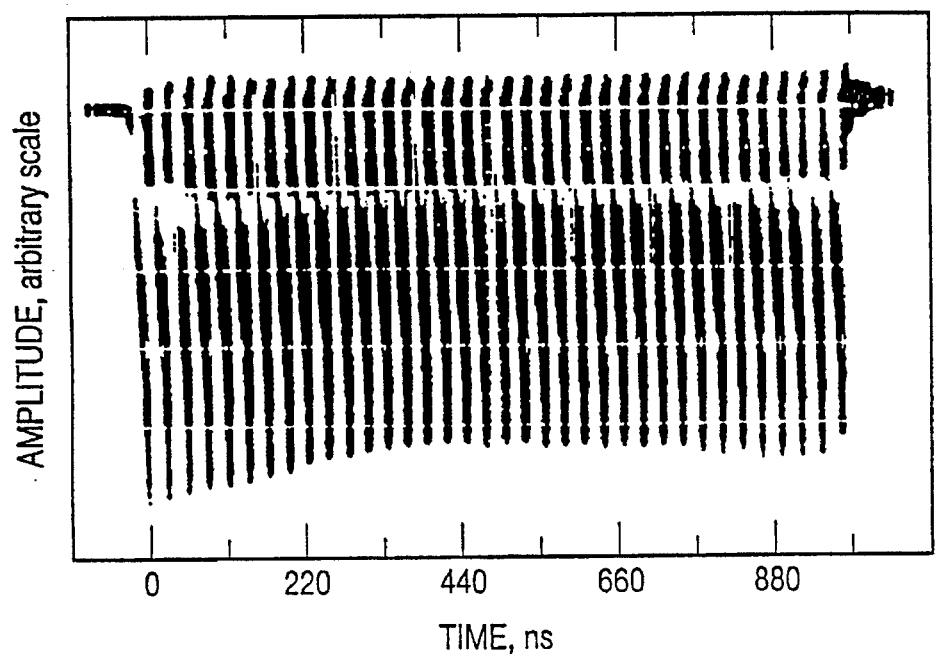
FIG. 5B shows the train when a variable neutral density filter is positioned into the expanding fan of output beams.

These cells performed as expected. FIG. 5 shows oscilloscope traces created by a train of pulses exiting the 2–m cell. Pulsed radiation supplied by the second harmonic output of a Nd:YAG laser was introduced into the cell. A converging lens, placed at the focal plane of the output coupler, focused all the output beams onto a single photodiode with a 1 ns risetime. The 350-MHz-bandwidth oscilloscope measured a pulsewidth of 7.5 ns (FWHM). The 36 pulses shown in the trace span 948 ns and were created over a path length of >280 m. Aperturing the input beam between 2 and 6 mm diameter did not change the relative intensity of the pulses in the train. The ratio of the last-to-first pulse amplitude in FIG. 5A indicates that the reflectivity of the coatings on mirrors B and A' is 0.995 since the measured output-coupler reflectivity is 0.968 at 532 nm. Inserting a neutral density filter that has a linearly varying optical density in the fan of output beams resulted in the trace shown in FIG. 5B. The proper location of the filter was easily identified by coarsely positioning the filter in the fan of output beams while observing the pulse train on the oscilloscope. The spatial separation between the pulses 32.6 cm from the output coupler (near the focal plane) was measured to be 1.0 mm, in agreement with Eq. 2.

Tomography Ring 4: In practice, it will seldom be necessary to require more projection angles than projection elements for artifact-free imaging. Thus, letting $N_f$=$n_d$, Eqs. 5–7 completely specify the parameters of the instrument for a required flow diameter and resolution. For example, for a 10-cm-diam flow, a resolution of 1 mm, and a fan angle of 30°, we find F=3.86, R=19.32 cm, w=2 mm, $N_d$=606.9, $n_d$=$N_f$=$N_d/N_a$=101.15, and $F_M$=16.86. Of course, $F_M$, $n_d$, $N_f$, and $N_d$ must be integers, and the tabulation given in Table I is useful for identifying the exact configuration for a given application. In the configuration shown in FIG. 4, $n_d$=$N_f$=96, $F_M$=16, 2r=10.16 cm (4 in.), and R=19.61cm. Then detector width is given by Eq. 8, viz., $$w = \frac{2(3.14)\left(\frac{10.16\text{ cm}}{2}\right)}{6(96)} \sqrt{\frac{2}{\left(1-\cos\left(\frac{180°}{6}\right)\right)}} = 0.21 \text{ cm.}$$

This configuration is shown in Table I by bold face type. Silicon photodiodes of greater than 4 mm area that have 1-ns risetimes, and responsivities greater than 0.1 A/W between 190 nm and 1.1 μm are widely available.

An easily replicated fan-beam generator consists of an UV transmitting optical fiber and an optic. Analysis of the capabilities of silica macrofibers for this application [E. J. Beiting, *Appl. Opt.* 31, 1328–1343 (1992)] indicates that the short-wavelength operating limit is limited by this component to 200 nm if a 200-μm-diameter fiber is used. Furthermore, a straightforward spherical-cylindrical lens combination coupled to this fiber produces an intensity profile with highly desirable characteristics. The intensity of an ideal fan varies exponentially as a function of the path length intercepted by a ray within the fan. Accordingly, for a constant absorption coefficient, each detector within the fan will see an equal intensity and the dynamic range will be maximized. Laboratory measurements of the intensity profile produced by this fiber-lens combination closely approximates this ideal. The spherical-cylindrical lens assembly is easily combined into a single micro-optic element.

Electronics 6: The most economical method to digitize the train of pulses emitted from each detector is to use fast sampling techniques and analog shift registers. For example, synchronizing the signal pulses to an 80-MHz clock allows the peak of each 5-ns pulse (separated by 12 ns) to be sampled. Laboratory tests (E. J. Beiting, *Opt. Lett.* 16, 1280 (1991)) using an inexpensive 640-cell integrated circuit confirmed the feasibility of digitizing such a pulse train. Such a system has 40 sets of 16-cell groups available for measurements of temperature, concentration of additional chemical species, fast series of reconstructions, or increased resolution.

Capability of System

To quantify the performance of the tomography ring system, a simplified test instrument was built with the specifications listed above. Here, a single fan beam source and 96 detectors were mounted on a 60° segment of a circle. Each detector was connected to a fast peak-and-hold circuit whose output was fed into a multiplexed 96-channel 12-bit analog-to-digital converter. A flow with a maximum diameter of 10 cm was rotated in the fan beam to create the multiple projections. The fan beam generator comprised a 400-μm-diam silica fiber, a 25 mm f.l. spherical microlens, and a –6.35 mm f.l. cylindrical microlens. Custom designed photodiodes of 2.1-mm width and 2.5 mm height were mounted abutting each other. Details of this device are published in E. J. Beiting, *Appl. Opt.* 31, 1328–1343 (1992).

Figure 6A:
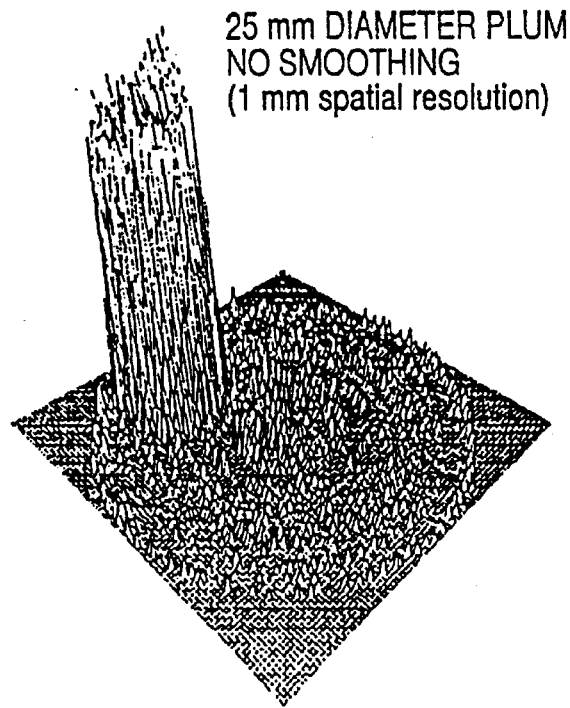
FIG. 6 is a concentration plot of 2.5 cm diameter plume of diacetyl located near the edge of a 10 cm diameter reconstruction zone, where each of the 96 projections was taken using a single pulse of radiation at 444 nm.
Figure 6B:
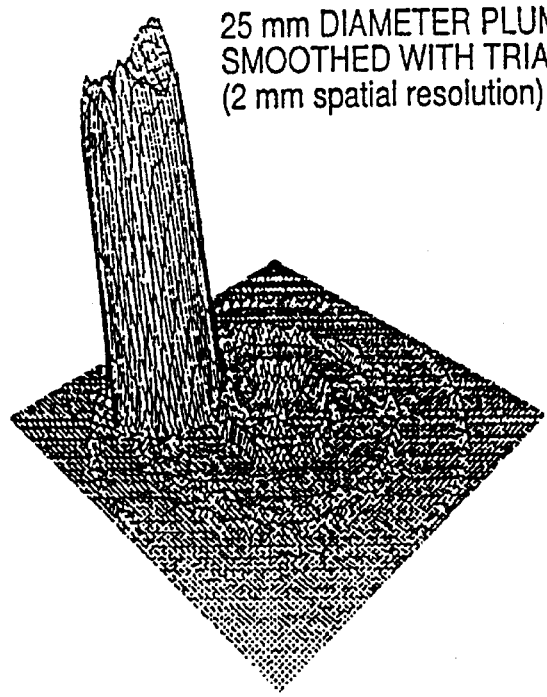

The reconstructions shown in FIG. 6A demonstrate the capability of the system. A boiling flask of diacetyl ($CH_3COCOCH_3$) was rotated in the fan near the edge of the 10-cm diam reconstruction zone. This created an unstable flow with a diameter of 2.5 cm. The average value of the CT numbers in the flow is $6 \times 10^{-2}$. CT numbers are the unitless product of the absorption coefficient and the pixel length (1.09 mm). The noise both in and out of the flow ($\approx 2.5 \times 10^{-3}$) is due to the flow and is not the noise limit of the instrument. The noise in this reconstruction is ~60% greater than that taken when the interprojection noise is largely uncorrelated and more than 400% higher than that taken the interprojection noise is highly correlated (see below.). These noise levels can be reduced further by using spatial averaging as demonstrated in FIG. 6B. The degree of correlation among the projections in the fast instrument depends on the method used to couple the output of the OPTG to the fibers. Simply placing the fibers in the outputs of the OPTG leads to uncorrelated projection noise. Coupling through fused fiber splitters (star couplers) can create correlations that lead to reconstructions with noise values between the correlated and uncorrelated values measured here.

The two principal measures of instrument performance are sensitivity and spatial resolution. Spatial resolution is a function of the number of projections and number of elements within a projection. However, both performance parameters are a function of noise since spatial resolution can be traded for increased sensitivity. Thus reconstruction noise is the principal measure of system performance. Noise in the reconstructed field is a function of the projection noise and the correlation of the noise within a projection.

The principal source of projection noise is due to laser speckle. This noise is caused by shot-to-shot variations in the speckle pattern on the surface of the detectors. The speckle is generate when coherent (laser) light passes through a multimode optical fiber. The speckle is the random pattern created by the constructive and destructive interference among the modes within the fiber. For monochromatic light, there is 100% contrast between light and dark segments; the contrast decreases with increasing bandwidth. Any phenomenon (fiber motion, convective refractive index variations, laser mode stability) that changes the pattern faster than the time required to acquire all of the projections increases the projection noise. The noise is a function of the relative size of the speckle grain to the size of the detector. Fine speckle patterns will generate less noise than coarse grain patterns. The linear dimension of the speckle grain size on the detectors is directly proportional to wavelength and varies inversely with the square of the fiber diameter.

Two types of speckle noise were measured using the test instrument. Stationary speckle noise is the shot-to-shot standard deviation measured when the optical fiber is not purposely moved between laser shots (projections). Dynamic speckle noise is the shot-to-shot standard deviation measured when the fiber is flexed between laser shots. Both types of noise were found to be independent of intensity. These measurements were made using the second harmonic of a Nd:YAG laser that had a stable transverse mode and that could be operated with 1.0 $cm^{-1}$ and 0.003 $cm^{-1}$ bandwidths at 532 nm, and a laser dye oscillator operated at 444 mm that had a very unstable mode.

Table II presents a comparison of the projection noise, linear correlation coefficient which measures the correlation of the noise between detectors within a projection, and reconstruction noise for representative data. The projection noise-for the static fiber is highly correlated and its value is considerably less than that measured for the dynamic fiber. Moving the fiber between acquiring the projections largely uncorrelates the data. K. E. Bennett and R. L. Byer, *J. Opt. Soc. Am.* A 3, 624 (1986), presented a careful study of the relationship between the projection noise and reconstruction noise. The last column in Table II lists the ratio of the reconstruction noise measured here with that predicted with their theory for uncorrelated noise. This ratio increases as the correlation coefficient decreases and approaches 1 as the correlation coefficient approaches zero, in agreement with the theory. Correlated projection noise results in less reconstruction noise than uncorrelated projection noise of the same magnitude. The projection noise was found to decrease, and the correlation coefficient increase, with increasing detector size. Thus, increasing the detector size is an effective method of reducing the reconstruction noise caused by speckle.

These noise values in Table II are used to predict the sensitivity of the instrument to a chemical species in a practical environment. For example, consider the hydroxyl radical in an atmospheric pressure flame. Transitions originating from the $F_1$, J=1.5 level are relatively temperature insensitive. The $^PP_{11}$ transition from this level at 308 nm has an effective cross section $q_{eff}$ (half the peak value) of $6.9 \times 10^{-15}$ $cm^2$. For a signal-to-noise ratio of 1, minimum detectivity is $$n_0 = \frac{Q(T)}{g_J \exp(-E_J/kt)} \frac{\sigma_{noise}}{q_{eff}l} \quad (9)$$

$$= 5.36 \times 10^{16} \sigma_{noise} \quad (cm^{-3})$$

where $E_J$ is the energy and $g_J$ is the statistical weight of the level, Q(T) is the partition function, T is temperature, and $\sigma_{noise}$ is the reconstruction noise taken from Table II. The numerical value is calculated for the test geometry and for a flow at a temperature of 1000K. Considering the reduced number density at this temperature in a constant pressure flame, this represents a sensitivity of 5 ppm for the stationary fiber (correlated noise) and 15 ppm for the moving fiber (uncorrelated noise) for a spatial resolution of 1 mm. Increasing the dynamic range of the instrument may be achieved by simultaneously sampling the $^RR_{11}$ transition at 307 nm from the same energy level. This transition has an absorption cross section 30 times less than that of the $^PP_{11}$ transition.

In the fast instrument, a single pulse from a tunable laser is routed to the OPTG to create a series of pulses equally spaced in time. Each of these pulses is subsequently sent to the (six) source positions on the ting that are to be simultaneously activated. If these positions are activated using independent fibers, the projection noise will be largely uncorrelated and the reconstruction noise is approximated by the values measured using he dynamic fiber. If star couplers are used, correlations can be introduced leading to reconstructions with noise values between the static and dynamic values listed in Table II.

The proposed tomography method avoids the problem collisional quenching by measuring the amount of light absorbed directly by $N_0$. By measuring the transmitted light on a linear detector at many angles that are equally spaced around the flow, a cross sectional image of the concentration can be reconstructed using tomographic algorithms. Accordingly, quantitative cross sectional fields of chemical and physical parameters can be reconstructed because the data are straightforward to interpret. Furthermore, tomography has the experimental advantage that optical access outside the plane of observation is not required to collect the data. This is not true for PLIF.

This time-multiplexed design is highly versatile. A single pulse of light introduced into the OPTG will allow the quantitative imaging of the concentration of a chemical species. If a second spectral line is probed by introducing a second pulse into the OPTG at a different wavelength, both the temperature and the concentration of the species can be measured. If this second wavelength is chosen to probe a transition with an absorption cross section differing from that of the first transition by a factor equal to the dynamic range of the concentration achievable using a single wavelength, the dynamic range is increased to the square of the original value. A third sequence of pulses allows the concentration of another species to be measured, etc. Or, the second sequence of pulses can be used to obtain a second "snapshot" of the same species at a later time, thus tracing the time evolution of the flow. Thus the instrument is easily scalable to higher resolution, greater dynamic range, multi-species detection, or to a configuration that allows the temporal development of turbulent structure to be viewed through a series of fast snapshots.

It should be evident to one skilled in the art that many changes and modifications can be made in the configuration or uses of the fast optical tomographic imager without departing from the spirit of the present invention.

TABLE I

Instrument Parameters[a]

(A)

| | | d = 10 cm | |
|---|---|---|---|
| $\theta_{fan}$ | F | R (cm) | D (cm) |
| 30° | 3.864 | 19.32 | 38.6 |
| 45° | 2.613 | 13.07 | 26.1 |
| 60° | 2.000 | 10.0 | 20.0 |

(B)

| | | | | | | | | d = 10 cm | | | | | |
|---|---|---|---|---|---|---|---|---|---|---|---|---|---|
| | | $F_M$ | | | $N_d$ | | | w (cm)[b] | | | Number of pixels[c] | | |
| $N_f, n_d$ | $\theta_{fan} =$ | 30° | 45° | 60° | 30° | 45° | 60° | 30° | 45° | 60° | 30° | 45° | 60° |
| 12 | | 2 | 3 | 4 | 72 | 48 | 36 | 1.686 | 1.711 | 1.745 | 141 | 136 | 131 |
| 24 | | 4 | 6 | 8 | 144 | 96 | 72 | 0.843 | 0.855 | 0.873 | 563 | 547 | 525 |
| 36 | | 6 | 9 | 12 | 216 | 144 | 108 | 0.562 | 0.579 | 0.582 | 1266 | 1230 | 1182 |
| 48 | | 8 | 12 | 16 | 288 | 192 | 144 | 0.421 | 0.428 | 0.436 | 2251 | 2186 | 2101 |
| 60 | | 10 | 15 | 20 | 360 | 240 | 180 | 0.337 | 0.342 | 0.349 | 3518 | 3416 | 3283 |
| 72 | | 12 | 18 | 24 | 432 | 288 | 216 | 0.281 | 0.285 | 0.291 | 5066 | 4920 | 4227 |
| 84 | | 14 | 21 | 28 | 504 | 336 | 252 | 0.241 | 0.244 | 0.249 | 6895 | 6696 | 6434 |
| 96 | | 16 | 24 | 32 | 576 | 384 | 288 | 0.211 | 0.214 | 0.218 | 8985 | 8746 | 8404 |
| 108 | | 18 | 27 | 36 | 648 | 432 | 324 | 0.187 | 0.190 | 0.194 | 11,398 | 11,069 | 10,636 |
| 120 | | 20 | 30 | 40 | 720 | 480 | 360 | 0.169 | 0.171 | 0.175 | 14,072 | 13,666 | 13,131 |
| 132 | | 22 | 33 | 44 | 792 | 528 | 396 | 0.153 | 0.156 | 0.159 | 17,027 | 16,535 | 15,889 |

[a]The experimental configuration values shown in bold face.
[b]Scales linearly with flow diameter.
[c]Scales quadratically with flow diameter.

TABLE II

System Noise Study

| Conditions | Projection noise (%)[a] | Correlation coefficient | Reconstruction noise × 10³ | Ratio[b] |
|---|---|---|---|---|
| 532 nm, 0.003 cm⁻¹, static fiber | 2.25 (0.4) | 0.6 | 1.4 | 0.93 |
| 532 nm, 1.0 cm⁻¹, static fiber | 2.6 (0.3) | 0.85 | 0.99 | 0.58 |
| 444 nm, 0.5 cm⁻¹, static fiber | 4.0 (0.4) | 0.8–1.0[c] | 0.60 | 0.23 |
| 532 nm, 0.003 cm⁻¹, dynamic fiber | 9.0 (0.5) | 0.1 | 5.4 | 0.90 |
| 532 nm, 1.0 cm⁻¹, dynamic fiber | 7.2 (0.5) | 0.1 | 3.9 | 0.82 |
| 444 nm, 0.5 cm⁻¹, dynamic fiber | 6.0 (0.5) | 0.5 | 1.8 | 0.45 |

[a]Standard deviation of percent projection noise calculated across the fan is presented in parentheses.
[b]Ratio = Measured reconstruction noise/predicted uncorrelated reconstruction noise.
[c]Peaked

What is claimed is:

1. A generator for generating a series of pulses, said generator comprising, pulsed source means for providing a pulse having a pulse shape and a maximum amplitude, reflecting means having a plurality of surfaces for receiving said pulse and reflecting said pulse off of said surfaces a plurality of reflections defining a path extending between said surfaces, said pulse does not retrace through any portion along said path when reflecting off of said plurality of surfaces, said pulse reflecting a plurality of reflections off of one point of one of said surfaces, and splitting means for splitting said pulse for each of said plurality of reflection off of said one point of said one surface of said surfaces and for providing said series of pulses each of which having said pulse shape with proportional amplitude to said maximum amplitude.

2. The generator of claim 1 wherein said each reflection off of said one surface defines a time duration corresponding to distance traveled along said path by said pulse between said each reflection, and said time duration being equal and said distance travel being equal for each successive pulse of said series of pulses to define a constant frequency of said series of pulses.

3. The generator of claim 1 further comprising, focusing means for receiving from said splitting means said plurality of pulses for said each reflection off of said one surface and for focusing said plurality of pulses at respective focal points.

4. The generator of claim 1 further comprising attenuating means for receiving from said splitting means said plurality of pulses and for varying said proportional amplitude of each pulse of said series of pulses to a constant amplitude.

5. The generator of claim 1 wherein said pulsed source means is a pulsed laser, and said pulse is a laser pulse having a pulse duration defined by said pulse shape, said laser pulse spatially converging and then spatially diverging after each of said reflections off of said one point, and being collimated before each of said reflections off of said one point.

6. A generator for generating a series of pulses, said generator comprising, pulsed source means for providing a pulse having a pulse shape and a maximum amplitude, a plurality of mirrors, one of which is an object mirror, a second of which is a conjugate mirror, and a third of which is a reflecting mirror, said mirrors receiving said pulse and reflecting said pulse off of said mirrors through a path extending between said mirrors, said pulse reflecting off each of said plurality of mirrors a plurality of reflections, said pulse does not retrace through any portion along said path, said pulse reflecting off of said three mirrors in sequence from said object mirror to said reflecting mirror to said conjugate mirror to said reflective mirror and back to said object mirror, said pulse reflects off of said object mirror at one object point, said pulse reflects off said conjugate mirror at one conjugate point, said pulse reflects off of said reflective mirror at differing reflecting points, said object mirror reflecting said pulses at differing reflecting angles at said one object point, said object mirror splitting by refraction said pulse at said one object point, at differing respective refracted angles, said splitting creating a reflected portion of said pulse and a refracted portion of said pulse producing successive pulses of said series of pulses decreasing in amplitude from said maximum amplitude while retaining said pulse shape.

7. The generator of claim 6 wherein time between each pulse of said series of pulses is equal.

8. The generator of claim 6 wherein said object mirror comprises an object focusing surface receiving and focusing said refractive portion of said pulse for said each reflection at said object point, said object focusing surface focusing said each successive pulse at differing respective object focal points.

9. The generator of claim 6 wherein, said object mirror comprises an object focusing surface receiving and focusing said refractive portion of said pulse for said each reflection at said object point, said object focusing surface focusing said each successive pulse at differing respective object focal points, said conjugate mirror reflects said pulse at differing reflecting angles at said one conjugate point, said conjugate mirror splitting by refraction said pulse at said one conjugate point at differing respective refracted angles, said splitting creating a reflected portion of said pulse and a refracted portion of said pulse producing successive pulses of said series of pulses decreasing in amplitude from said maximum amplitude while retaining said pulse shape, said conjugate mirror comprising a conjugate focusing surface for receiving and focusing said refractive portion of said pulse for said each reflection at said conjugate point, said conjugate focusing surface focusing said each successive pulse at differing respective conjugate focal points, and said series of pulses having decreasing amplitude and are alternately produced at said object focal points and said conjugate focal points.

10. A generator for generating a series of pulses, said generator comprising, pulsed source means for providing a pulse having a pulse shape and a maximum amplitude, and a first and third mirror opposing a second and forth mirror, said pulse reflects off of all of said four mirrors in sequence, said mirrors receiving said pulse and reflecting said pulse off of said mirrors through a path extending between said mirrors, said pulse reflecting off each of said mirrors a plurality of reflections, said pulse does not retrace through any portion along said path, said pulse reflecting off of said mirrors in sequence from said first mirror to said second mirror to said third mirror to said forth mirror and back to said first mirror, said first mirror has a reflecting surface reflecting at differing reflection angles said pulse at one point, said first mirror splitting by refraction said pulse at said one point at differing respective refracted angles, said splitting creating a reflected portion of said pulse and a refracted portion of said pulse causing each successive pulse of said series of pulses to decrease in amplitude from said maximum amplitude while retaining said pulse shape, and focusing means for receiving and focusing said refractive portion of said pulse for said each reflection on said one point of said first mirror, said focusing means focusing said each successive pulse at differing respective focal points.

11. The generator of claim 10 wherein time between each pulse of said series of pulses is equal.

* * * * *

UNITED STATES PATENT AND TRADEMARK OFFICE
CERTIFICATE OF CORRECTION

PATENT NO. : 5,579,166
DATED : November 26, 1996
INVENTOR(S) : Edward J. Beiting It is certified that error appears in the above-indentified patent and that said Letters Patent is hereby corrected as shown below:

On the title page, insert the following:
[73] Assignee: The Aerospace Corporation, El Segundo, Calif.

Signed and Sealed this

Twenty-ninth Day of July, 1997

Attest:

BRUCE LEHMAN

*Attesting Officer*    *Commissioner of Patents and Trademarks*